(12) United States Patent
Kolli

(10) Patent No.: US 11,761,068 B2
(45) Date of Patent: Sep. 19, 2023

(54) 3D PRINTABLE STAINLESS STEEL ALLOY WITH ANTIBACTERIAL PROPERTIES FOR ORTHOPEDIC IMPLANTS

(71) Applicant: Blue Point Materials Research LLC, Herndon, VA (US)

(72) Inventor: Ratna Prakash Kolli, Herndon, VA (US)

(73) Assignee: Blue Point Materials Research LLC, Herndon, VA (US)

( * ) Notice: Subject to any disclaimer, the term of this patent is extended or adjusted under 35 U.S.C. 154(b) by 0 days.

(21) Appl. No.: 17/100,217

(22) Filed: Nov. 20, 2020

(65) Prior Publication Data

US 2021/0156015 A1 May 27, 2021

Related U.S. Application Data

(60) Provisional application No. 62/939,379, filed on Nov. 22, 2019.

(51) Int. Cl.
*C22C 38/00* (2006.01)
*B22F 10/00* (2021.01)
(Continued)

(52) U.S. Cl.
CPC .............. *C22C 38/002* (2013.01); *B22F 1/05* (2022.01); *B22F 1/052* (2022.01); *B22F 9/08* (2013.01);
(Continued)

(58) Field of Classification Search
CPC ...... C22C 38/58; C22C 38/001; C22C 38/002; C22C 38/02; C22C 38/42; C22C 38/44;
(Continued)

(56) References Cited

U.S. PATENT DOCUMENTS 6,306,341 B1 10/2001 Yokota et al.
9,719,160 B1 8/2017 Gojny et al.
(Continued)

FOREIGN PATENT DOCUMENTS

CN 107419234 A * 12/2017 ............ B22F 3/1055
CN 108728773 A * 11/2018 ............ C21D 6/004

*Primary Examiner* — Anthony M Liang
*Assistant Examiner* — Danny N Kang
(74) *Attorney, Agent, or Firm* — BEKIARES ELIEZER LLP

(57) ABSTRACT

An austenitic stainless steel alloy having antibacterial properties, corrosion resistance properties, and good hardness and strength is provided. A method of manufacturing by gas atomization, metal additive manufacturing, and heat treatment is also provided. The stainless steel alloy composition and powder consisting of chromium (Cr), molybdenum (Mo), manganese (Mn), nickel (Ni), copper (Cu), silicon (Si), nitrogen (N), carbon (C) and iron (Fe) is described. The alloy can be processed into spherical powder by gas atomization or other methods suitable for metal additive manufacturing or metal 3D printing. The powder can be processed by metal additive manufacturing into articles. Heat treatment promotes the formation of copper nanoprecipitates leading to excellent antibacterial properties and good mechanical properties. The constituent elements of the alloy provide for good corrosion resistance.

12 Claims, 8 Drawing Sheets

(51) Int. Cl.
*B22F 1/05* (2022.01)
*B22F 9/08* (2006.01)
*B33Y 10/00* (2015.01)
*B33Y 70/00* (2020.01)
*B33Y 80/00* (2015.01)
*C22C 38/58* (2006.01)
*C22C 38/44* (2006.01)
*C22C 38/02* (2006.01)
*C21D 9/00* (2006.01)
*C22C 38/42* (2006.01)
*B22F 1/052* (2022.01)
*B22F 1/065* (2022.01)

(52) U.S. Cl.
CPC ............... *B22F 10/00* (2021.01); *C21D 9/00* (2013.01); *C22C 38/001* (2013.01); *C22C 38/02* (2013.01); *C22C 38/42* (2013.01); *C22C 38/44* (2013.01); *C22C 38/58* (2013.01); *B22F 1/065* (2022.01); *B22F 2304/10* (2013.01); *B33Y 10/00* (2014.12); *B33Y 70/00* (2014.12); *B33Y 80/00* (2014.12)

(58) Field of Classification Search
CPC .......... C22C 33/0285; B22F 1/05; B22F 9/08; B22F 10/00; B22F 2304/10; B22F 1/065; B22F 1/052; B22F 10/34; B22F 10/64; B22F 2009/0824; B22F 2999/00; B22F 9/082; B22F 10/25; B22F 10/28; C21D 9/00; B33Y 10/00; B33Y 70/00; B33Y 80/00; B33Y 40/20; A61B 17/58; A61B 17/866; Y02P 10/25
See application file for complete search history.

(56) References Cited

U.S. PATENT DOCUMENTS

2007/0181221 A1    8/2007   Pickford et al.
2007/0287027 A1   12/2007   Justin et al.
2013/0092296 A1    4/2013   Qui
2016/0250394 A1    9/2016   Pawar et al.

\* cited by examiner

3D PRINTABLE STAINLESS STEEL ALLOY WITH ANTIBACTERIAL PROPERTIES FOR ORTHOPEDIC IMPLANTS

CROSS-REFERENCE TO RELATED APPLICATIONS

This application claims priority to and the benefit of U.S. Provisional Patent Application No. 62/939,379, filed Nov. 22, 2019, the contents of which are incorporated herein by reference.

BACKGROUND AND SUMMARY OF THE INVENTION

The present invention relates to an austenitic stainless steel alloy (SS Alloy) with antibacterial properties, corrosion resistance, and mechanical properties. The stainless steel alloy can be processed into spherical powder for use in metal additive manufacturing or metal 3D printing. The powder can be processed into articles, such as surgical implants and tools by metal additive manufacturing or other methods.

One common cause of surgical implant failure is development of post-operative infections at the bone repair site. Infections after surgical implant procedures are caused by bacteria with the most common one being *Staphylococcus aureus* (*S. aureus*). But other gram-positive or gram-negative infectious bacteria can also cause surgical site infections. The bacteria adhere to implant surfaces and then accumulate and colonize the implant surfaces. This can lead to significant complications in the patient including chronic inflammation, osteomyelitis (bone infection), sepsis (systemic infection in the bloodstream) and inhibition of bone healing leading to failure of the implant. In addition, considerable costs, and longer hospital stays may result due to infection at surgical sites.

Cure of an infected bone repair site requires, at a minimum, administration of a long course of antibiotics. In many cases a cure requires additional surgical procedures for removal and replacement of the fixation implant or devices. Furthermore, considerable costs, longer recovery times and repeated hospital stays may result due to infection at bone repair sites. In the U.S. alone, at least 135,000 of the over 2.35 million fixation implants and devices annually develop a post-operative infection. It is estimated that the costs for treating these infections ranges from $5,000 to $50,000+ depending on the type of bone repair surgery and specific implant or device. There is a very high failure rate associated with initial infection treatment. Failure of the first course of treatment in turn results in a high failure rate of subsequent courses thereby multiplying costs.

The austenitic stainless steel referred to as 316L stainless steel (316L SS) is an alloy commonly used in surgical implants and tools. The advantages associated with the use of 316L SS are the fact that it is relatively inexpensive, easily available, has excellent fabrication properties, is biocompatible, has good strength and exhibits acceptable corrosion resistance. The majority of internal fixation implants and devices are currently made from 316L stainless steel. These implants and devices can be roughly classified into a few major categories, which include wires, pins, screws, plates, and intramedullary nails or rods. However, Type 316L SS demonstrates no known antibacterial properties. One common remedy for this problem is surface modification of the metal implant by providing a metallic coating with antibacterial properties. The antibacterial properties of metallic elements such as silver, copper, zinc, and the more costly gold, platinum, palladium, and others are well documented in the literature.

Antibacterial coatings on metallic surgical implant alloys are known in the prior art as illustrated by several examples. In U.S. Patent Publication No. US 2016/0250394 A1, Pawar et al. describe a method for incorporating a silver or copper outer layer into a biomedical implant providing antibacterial properties. In U.S. Patent Publication No. US 2007/0287027 A1 to Justin et al., a method to deposit an antimicrobial metallic material on metal surfaces was taught. In U.S. Patent Publication No. US 2007/0181221 A1 to Pickford et al., a method is provided in which a metal implant for use in a surgical procedure is imparted with a surface layer that is integral with the metal substrate, and which incorporates a biocidal material. But, in general, coating methods suffer from several deficiencies that reduce their effectiveness including concentration fluctuations of the agent in a coating, durability deficiencies causing flaking of the coating, and cytotoxicity issues due to locally high antibacterial agent concentrations. This approach is also relatively expensive due to extra steps required for processing.

In the prior art we also find that metallic elements with antibacterial properties are included as a constituent of some stainless steels and other alloys to achieve antimicrobial effects. This is exemplified by U.S. Pat. No. 9,719,160 B1 to Gojny and Sun who discuss a 304-type austenitic stainless steel with antibacterial properties. In U.S. Patent Publication No. US 2013/0092296 A1 to Qui et al. a martensitic antibacterial stainless steel is presented. In U.S. Pat. No. 6,306,341 B1 to Yokata et al. a method is provided for a stainless steel product with antimicrobial activity. Notably, these stainless steels are not suitable as surgical implant or tool materials. Some of the stainless steels contain metallic elements such as vanadium, tin, rare earth elements and others that result in cytotoxicity issues or biocompatibility issues. Additionally, some of the stainless steels have lower or insufficient corrosion resistance.

The present invention of austenitic stainless steel alloy has metallic alloying elements that provide for antibacterial properties, good hardness and strength, and good corrosion resistance. The stainless steel alloy according to the present invention not only has improved antibacterial properties over conventional materials, but also it is 3D printable, which greatly enhances its usefulness. This antibacterial stainless steel alloy has the ability to be processed by gas atomization or other methods into spherical powder, and subsequently processed by powder bed or powder deposition metal additive manufacturing methods into articles. Heat treatment results in nanoprecipitation increasing the antibacterial properties and good mechanical properties of the stainless steel alloy. Elements are included for good corrosion resistance. Quantitative assays demonstrate a bacteriostatic and bactericidal effect on infectious bacteria such as *Staphylococcus aureus*. Mechanical property testing illustrates the ability to increase hardness and strength. Tensile testing also demonstrates a good combination of high strength and ductility. Corrosion testing results demonstrate the ability to resist corrosion in a physiological environment.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
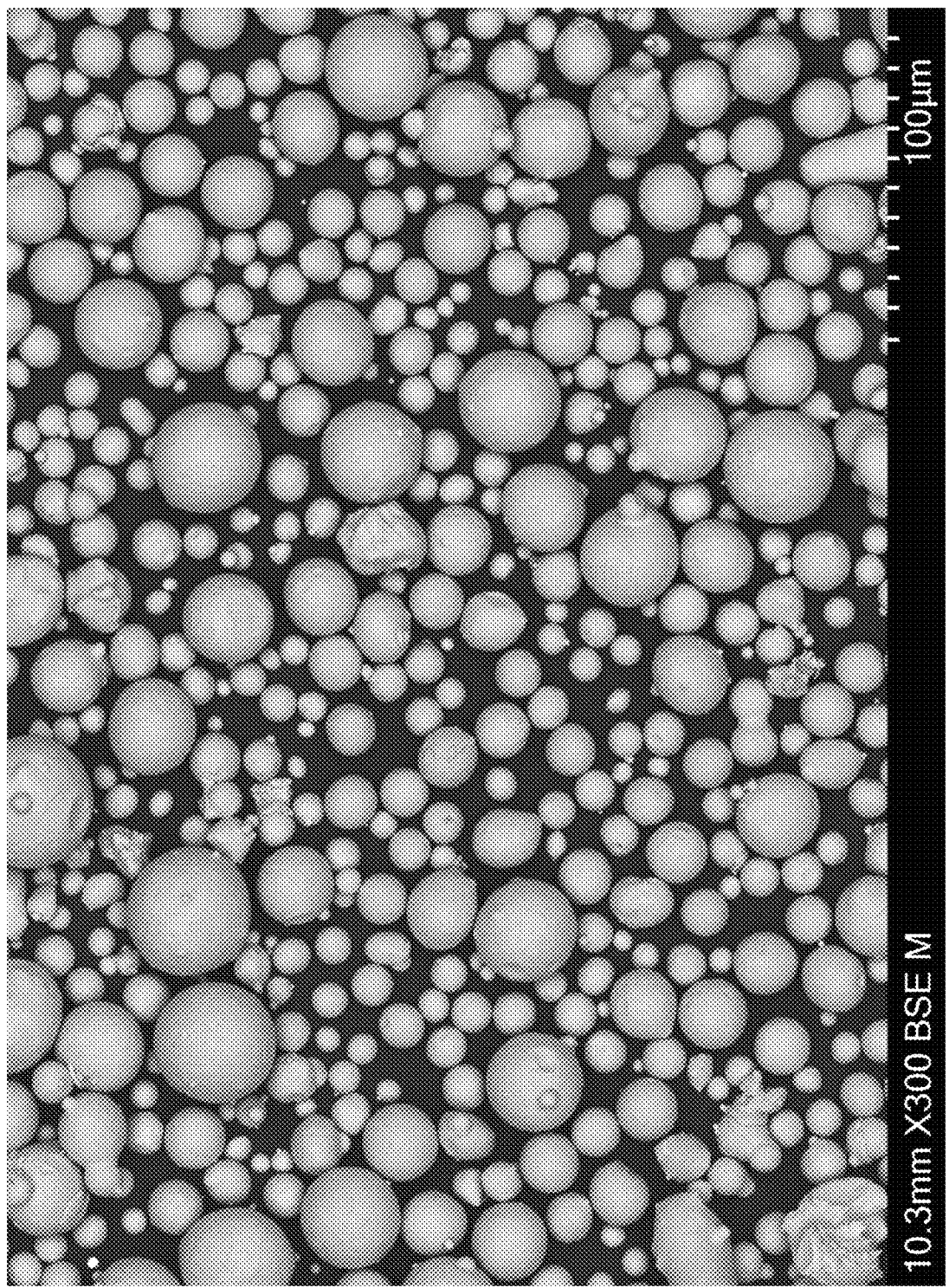
FIG. 1 shows the antibacterial stainless steel alloy powder after gas atomization.

An austenitic stainless steel alloy with antibacterial properties, corrosion resistance properties, good hardness and strength, and its ability to be printed by metal additive manufacturing are described. In addition to metal 3D printing, the alloy can be processed by casting, forging, and other conventional methods. The alloy can be thermally treated to increase antibacterial properties and also the hardness and strength. The alloy has good corrosion resistance. The antibacterial stainless steel alloy is comprised of 3.5-4.5 weight % copper, 18.0-20.0 weight % chromium, 14.0-16.0 weight % nickel, 2.5-3.0 weight % molybdenum, 0.08-0.12 weight % nitrogen, ≤2.0 weight % manganese, ≤0.75 weight % silicon, ≤0.02 weight % carbon, trace quantities of ≤0.025 weight % phosphorous and ≤0.01 weight % sulfur, and the balance is iron.

Copper is included in concentrations from 3.5-4.5 wt. % due to its antibacterial properties and ability to increase hardness and strength. Copper is believed to possess antibacterial activity to gram-positive or gram-negative bacteria. It is believed that the possible mechanisms include reduction-oxidation (redox) activity damaging cellular macromolecules, non-specific binding to proteins that interfere with normal cellular function, and binding to metabolic enzymes that inhibits metabolic processes and alters normal cellular functions. If the copper concentration is too low, then the antibacterial properties are not exhibited. Copper is also an austenite forming element promoting the formation of the γ-phase in stainless steels. Copper also has ability to increase hardness and thus strength through nanoprecipitation if included in sufficient quantities. Copper can also improve corrosion resistance of an alloy. Too high a concentration of copper can lead to problems with corrosion resistance.

Nitrogen is included in concentrations ranging from 0.08 to 0.12 wt. % since it is a very strong austenite stabilizer and enhances corrosion resistance. The element promotes the formation of the γ-phase. In particular, nitrogen in small concentrations is very effective in improving pitting corrosion resistance and crevice corrosion resistance. It is believed that nitrogen acts to strengthen the passivated layer, increases the chromium concentration in the layer, and possibly binds with hydrogen or chlorine. The presence of nitrogen also acts to increase hardness and strength. Excessive nitrogen content is undesirable as it may promote the formation of undesirable nitrides or reduce ductility.

Chromium is included in concentrations ranging from 18.0 to 20.0 wt. % to improve corrosion resistance. When chromium is added at concentrations greater than approximately 10.5 wt. % the corrosion resistance markedly increases. The corrosion resistance again increases at concentrations greater than over about 17.0 wt. %. The presence of chromium leads to the formation of a passivated layer of chromium oxide on the surface that resists uniform and localized corrosion.

Nickel is added in concentrations ranging from 14.0 to 16.0 wt. % to improve corrosion resistance and increase toughness and strength. At concentrations greater than about 8.0 wt. % nickel promotes the formation of the γ-phase and hence it is included as an austenite stabilizer.

Molybdenum is included in concentrations ranging between 2.5 wt. % and 3.0 wt. % to improve corrosion resistance, particularly pitting corrosion resistance. This element also increases strength. Too much molybdenum should not be used since it is expensive thereby increasing costs. Additionally, too high of a concentration of molybdenum is not desired since the element is a α-phase or ferrite former. Too high a concentration of molybdenum also promotes the formation of the detrimental intermetallic σ-phase.

Manganese is added in concentrations less than 2.0 wt. %. Manganese promotes the formation of the γ-phase and hence it is included as an austenite stabilizer. Manganese is also included since it forms manganese sulfide and thus it effectively ties up sulfur impurities. Manganese also increases hardness and strength. Manganese also has the beneficial effect of increasing the solubility of nitrogen.

Silicon is included in concentrations less than 0.75 wt. % since it is an effective deoxidizing agent. In this role it helps reduce defects. Silicon also acts to increase strength and hardness through solid solution strengthening.

The antibacterial stainless steel alloy powder may be produced by gas atomization using an inert gas such as nitrogen or argon. The powder may also be produced by plasma atomization or plasma rotating electrode processes. The resulting powder is a smooth and spherical powder with circularity near 1.0, a convexity near 1.0, and an apparent density suitable for metal additive manufacturing. A smooth and spherical powder will allow for good powder flowability and packing density suitable for metal additive manufacturing. The powder has an approximate range of particle diameters of 15 microns-45 microns for powder bed additive manufacturing and of approximately 44 microns-106 microns for powder deposition additive manufacturing. Powder that is irregularly shaped, rough, or has too broad a range of particle diameters may not have good flowability or packing density suitable for metal additive manufacturing.

The antibacterial stainless steel alloy powder may be processed by powder bed or powder deposition additive manufacturing methods into articles. Powder bed additive manufacturing methods include but are not limited to selective laser melting (SLM), selective laser sintering (SLS), direct metal laser sintering (DMLS) and e-beam melting (EBM). Powder deposition additive manufacturing methods include but are not limited to laser engineered net shaping (LENS). Alternatively, the antibacterial stainless steel alloy can be melted and processed by casting, forging, and other methods into articles.

The antibacterial stainless steel alloy may be thermally processed (heat treated) to promote the formation of homogeneously distributed nanoscale copper precipitates to increase hardness and strength and improve antibacterial performance. Thermal processing consists of two steps: a solution heat treatment followed by aging heat treatment. Solution heat treatment should occur at temperatures approximately between 1090° C. and 1110° C. for approximately 30 minutes to 60 minutes and then quenched in water at room temperature (e.g., 18° C. to 27° C., preferably 21° C. to 24° C.). If the solution treatment temperature is too high or the time is too long, then grain growth may occur. If the solution treatment temperature is too low, then any residual stresses or undesirable phases may not go into solution. Aging should occur at temperatures ranging from 600° C. to 750° C. for four to eight hours and quenched in water at room temperature (e.g., 18° C. to 27° C., preferably 21° C. to 24° C.). If the aging temperature is too low, then embrittlement may occur and if the aging temperature is too high then over aging may occur too quickly. An extended aging time duration will result in lower hardness and strength due to over aging of the nanoscale copper precipitates. An extended aging time may also lower corrosion resistance. Quenching during thermal treatment must be sufficiently fast to avoid formation of the detrimental sigma phase or chromium carbides. If quenching is too slow, such as in air, then these detrimental phases may form.

In one embodiment the antibacterial stainless steel alloy was produced in powder form by argon gas atomization. The composition in this example was approximately 19.45 weight % chromium, 14.89 weight % nickel, 3.95 weight % copper, 2.69 weight % molybdenum, 0.085 weight % nitrogen, 0.02 weight % manganese, 0.09 weight % silicon, 0.004 weight % carbon, trace quantities of phosphorous and sulfur, and the balance is iron.

FIG. 1 shows the antibacterial stainless steel alloy powder. The powder in this example had mean circularity of 0.976 and mean convexity of 0.998. The apparent density was 4.41 g/cm$^3$ and the Hall flow value was 13.41 s/50 g as determined by a Hall flowmeter. Laser size diffraction measurements illustrated that the powder had a Dv(10) of 17 microns, a Dv(50) of 28 microns and a Dv(90) of 45 microns indicating that the majority of the powder had particle diameter of between 17 microns and 45 microns. Sieve analysis of +53 microns and +45 microns showed 0 weight %.

Figure 2:
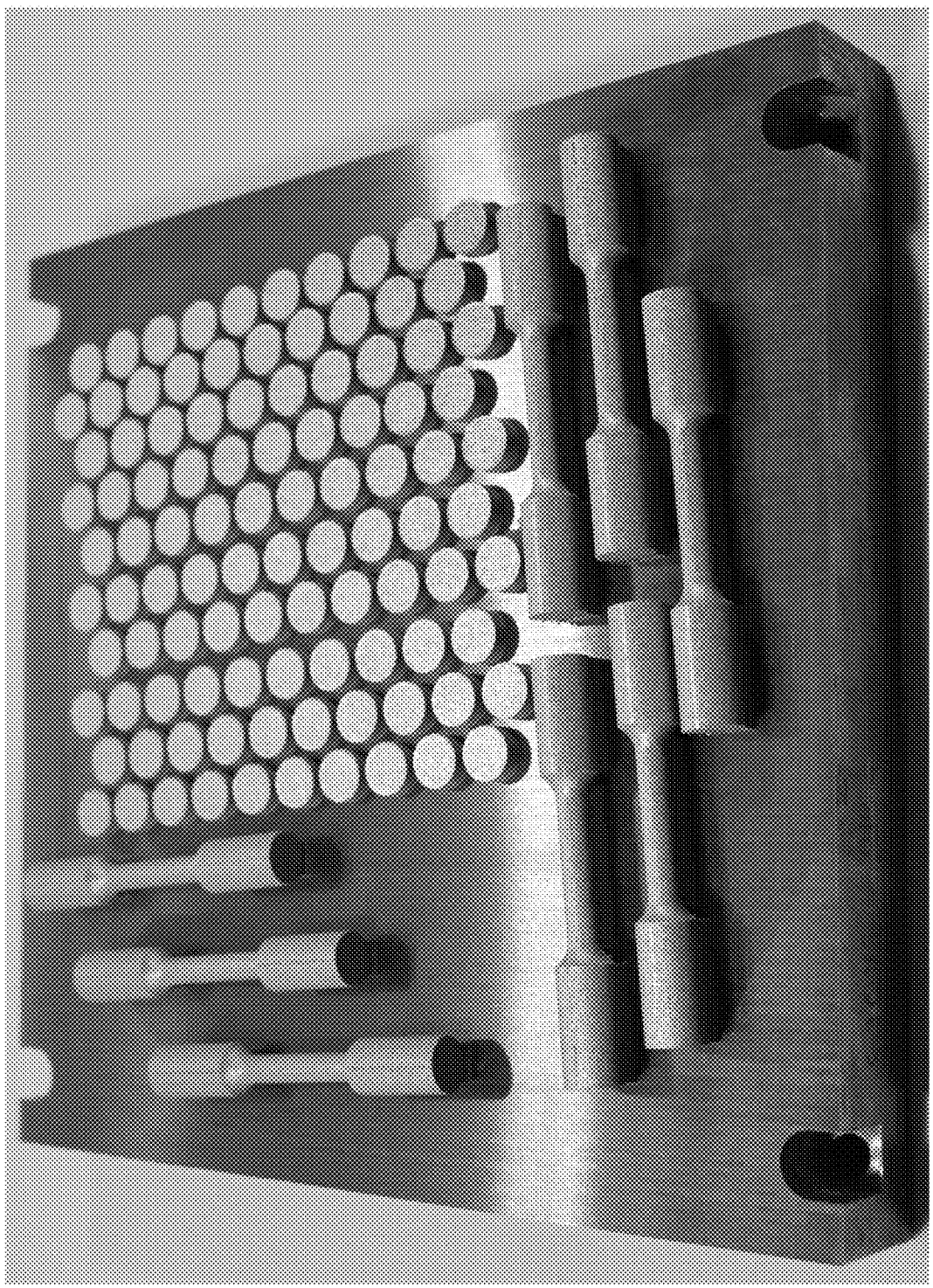
FIG. 2 illustrates the antibacterial stainless steel alloy powder processed by 3D printing into disks and rods.

The powder in this example was processed by DMLS using argon gas into test samples consisting of disks that are approximately 12.7 mm in diameter and tensile test specimen blanks. FIG. 2 shows the build plate containing the disks and tensile test specimen blanks.

The disks were cut from the build plate by wire electrical discharge machining (EDM) and then polished and cleaned in an alcohol rinse. The disks were solution heat treated at 1100° C. for approximately 30 minutes and then quenched in water at room temperature. Subsequently, the disks were subjected to aging heat treatment at 700° C. for four or six hours and quenched in water at room temperature.

The tensile test specimen blanks were cut from the build plate by wire EDM. They were then machined into tensile test specimens to meet the ASTM standard. The gauge length was approximately 25.4 mm (1-inch) and the gauge diameter was about 6.35 mm (0.25-inches).

For antibacterial testing of the antibacterial stainless steel alloy, a quantitative method following validated test protocols was used with a positive control of 99.9 wt. % copper (99.9% Cu) disks and a negative control of 316L stainless steel (316L SS) with no known antibacterial properties. The antibacterial stainless steel alloy test specimens and control specimens were in the form of 12.7 mm diameter disks that were approximately 4 mm thick. Antibacterial testing was performed using the *Staphylococcus aureus* bacteria. Before testing all test specimen disks and control disks were cleaned and sterilized in solution of 10% bleach/90% deionized water for 15 minutes and then autoclaved.

A 5 mL culture of *S. aureus* (Rosenbach ATCC 25923) was inoculated. The culture was diluted with media to 0.5 McFarland. The culture was diluted to create a starting inoculum of approximately $10^5$ cfu/mL. Ten microliters (10 μL) of the culture was placed on each test specimen disk and control disk and then covered with a sterile thin cover slip. Each disk was incubated at room temperature for 0.5, 2, 6 and 24 hours. Subsequently, each test specimen disk and control disk were separately placed into a 50 mL test tube with 5 mL of phosphate buffered saline (PBS) and 20 glass beads. The test tubes were vortexed for 30 seconds. One hundred microliters (100 μL) was taken from each test tube and serially diluted. Then 5 microliter (5 μL) drops from each dilution were placed onto Mueller-Hinton agar plates for a total of 5 replicates of each dilution per plate. The plates were incubated at 37° C. for 18 hours but no more than 24 hours to determine the number of surviving bacterial colonies.

Figure 3:
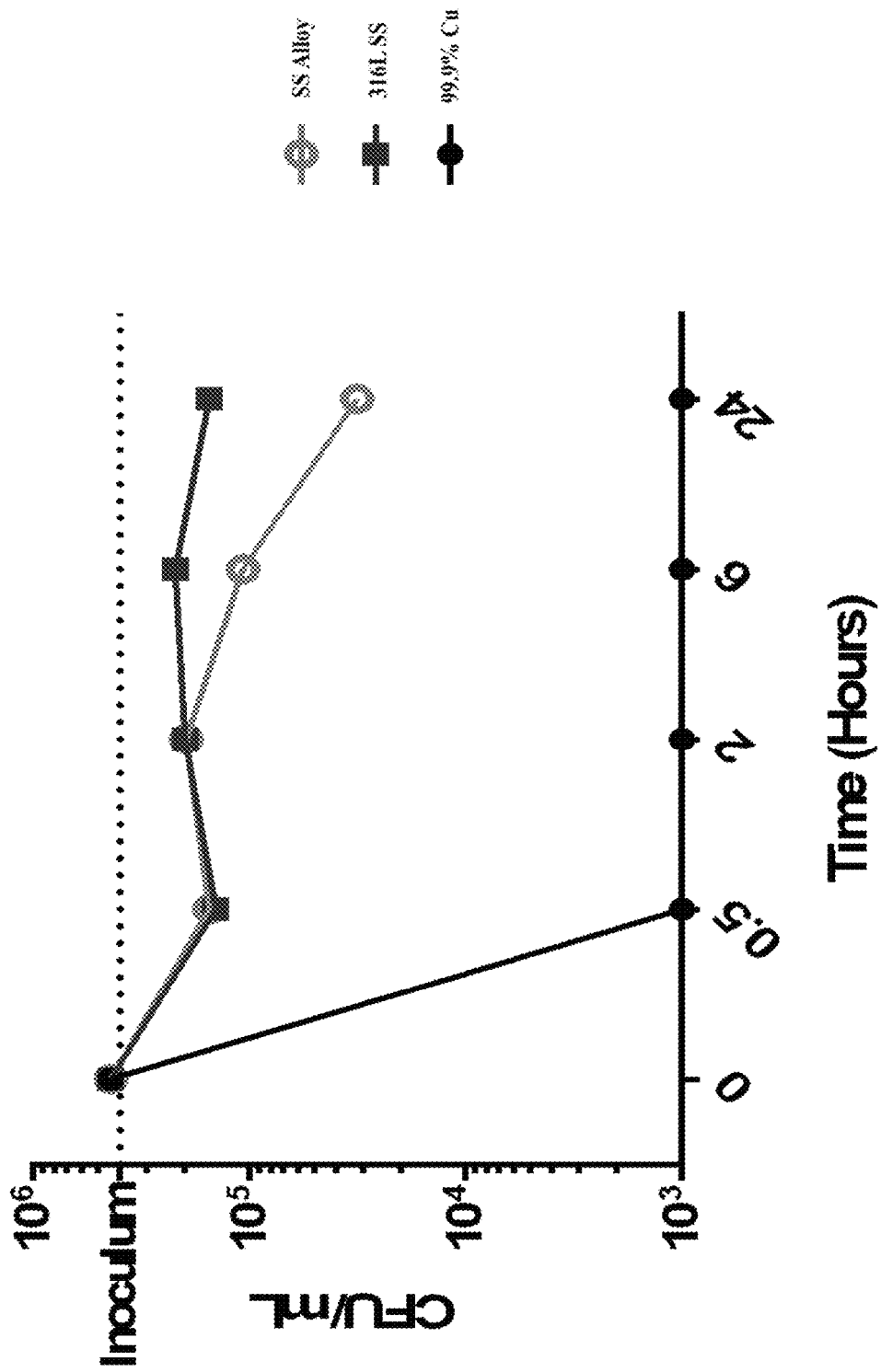
FIG. 3 illustrates the antibacterial property of the stainless steel alloy compared to positive and negative control materials.
Figure 4:
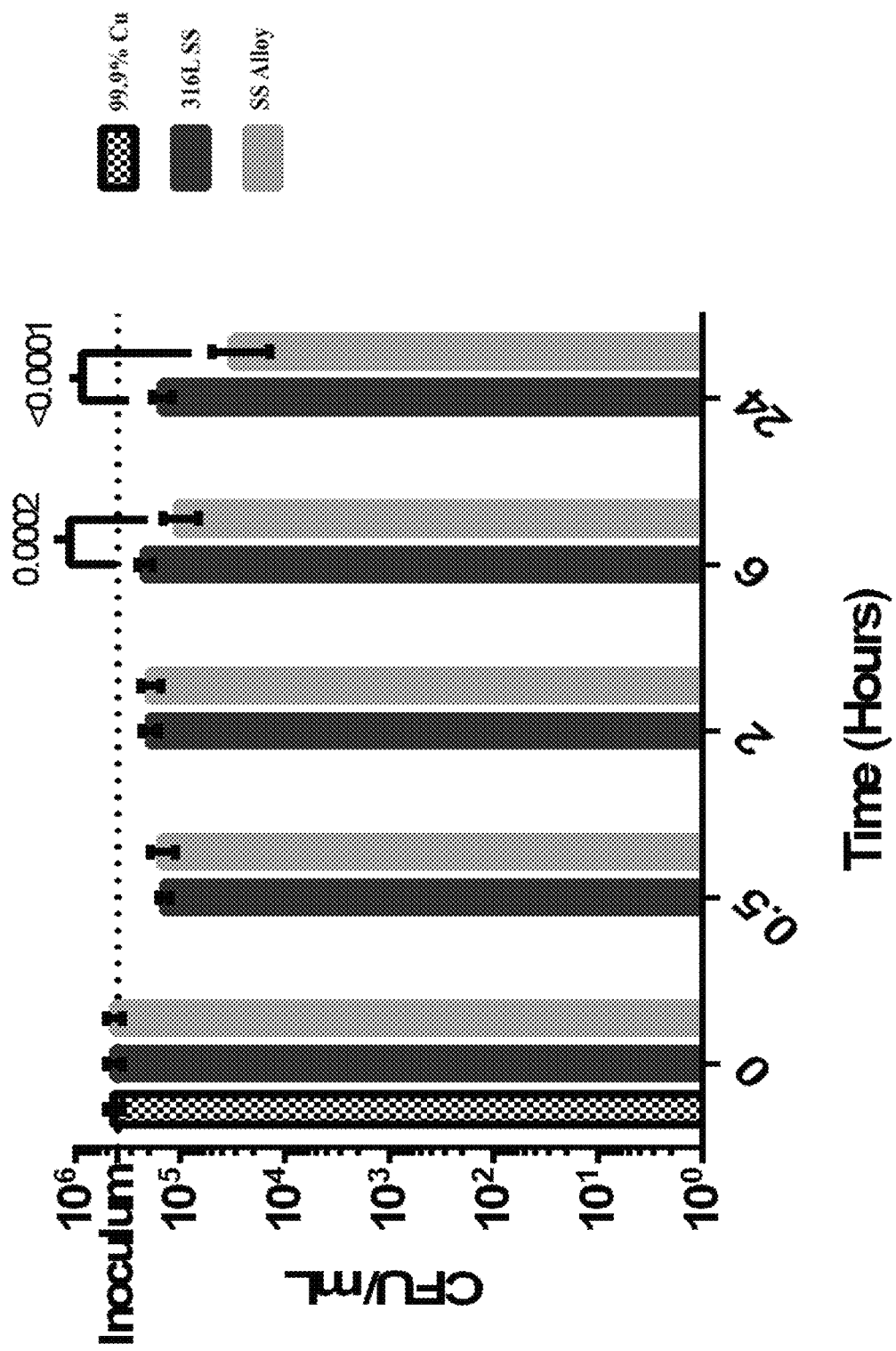
FIG. 4 shows a histogram of the average number of *S. aureus* bacterial colonies as a function of time comparing the antibacterial stainless steel alloy to the positive and negative control materials.
Figure 5:
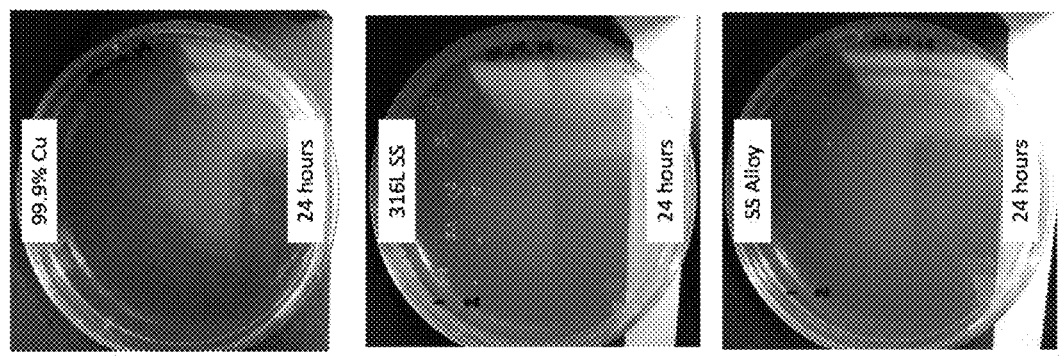
FIG. 5 exhibits the number of *S. aureus* bacterial colonies after 24 hours for the positive control material, negative control material, and antibacterial stainless steel alloy disks.

The number of surviving *S. aureus* bacterial colonies were counted and recorded for each disk at each time point. A graph of the results comparing the average number of *S. aureus* bacterial colonies as a function of time for the positive control, negative control, and the antibacterial stainless steel alloy disks is shown in FIG. 3. As shown in FIG. 3, the stainless steel alloy according to the present invention has significantly improved antibacterial properties. A histogram of the results along with the p-value for statistical significance are exhibited in FIG. 4. The number of *S. aureus* bacterial colonies for each of the 5 replicates after 24 hours for the positive control, negative control and antibacterial stainless steel alloy disks is shown in FIG. 4.

The antibacterial rate in percent after 24 hours was calculated by:

$$R = \frac{N_{control} - N_{test\ material}}{N_{control}} \times 100\%,$$

where R is the antibacterial rate, $N_{control}$ is the average number of bacterial colonies for the negative control disks, and $N_{test\ material}$ the average number of bacterial colonies for the antibacterial stainless steel alloy disks with antibacterial properties. The results are shown in Table 1.

TABLE 1

|  | Number of colonies at 0 hours (CFU/ml) | Number of colonies at 24 hours (CFU/ml) | 24 Hour Antibacterial Rate (%) |
|---|---|---|---|
| Antibacterial Stainless Steel Alloy | $4.40 \times 10^5$ | $3.20 \times 10^4$ | 79.2% |

Hardness of the antibacterial stainless steel alloy disks in Vickers Microhardness were measured following ASTM procedures. The results are shown in Table 2.

TABLE 2

| | Vickers Microhardness After Solution Treatment (1100° C. for 30 min) | Vickers Microhardness After Aging Treatment (700° C. for 4 hours) | Vickers Microhardness After Aging Treatment (700° C. for 6 hours) |
|---|---|---|---|
| Antibacterial Stainless Steel Alloy | 183.7 ± 1.8 HV/1 | 199.0 ± 2.3 HV/1 | 194.0 ± 4.9 HV/1 |

Figure 6:
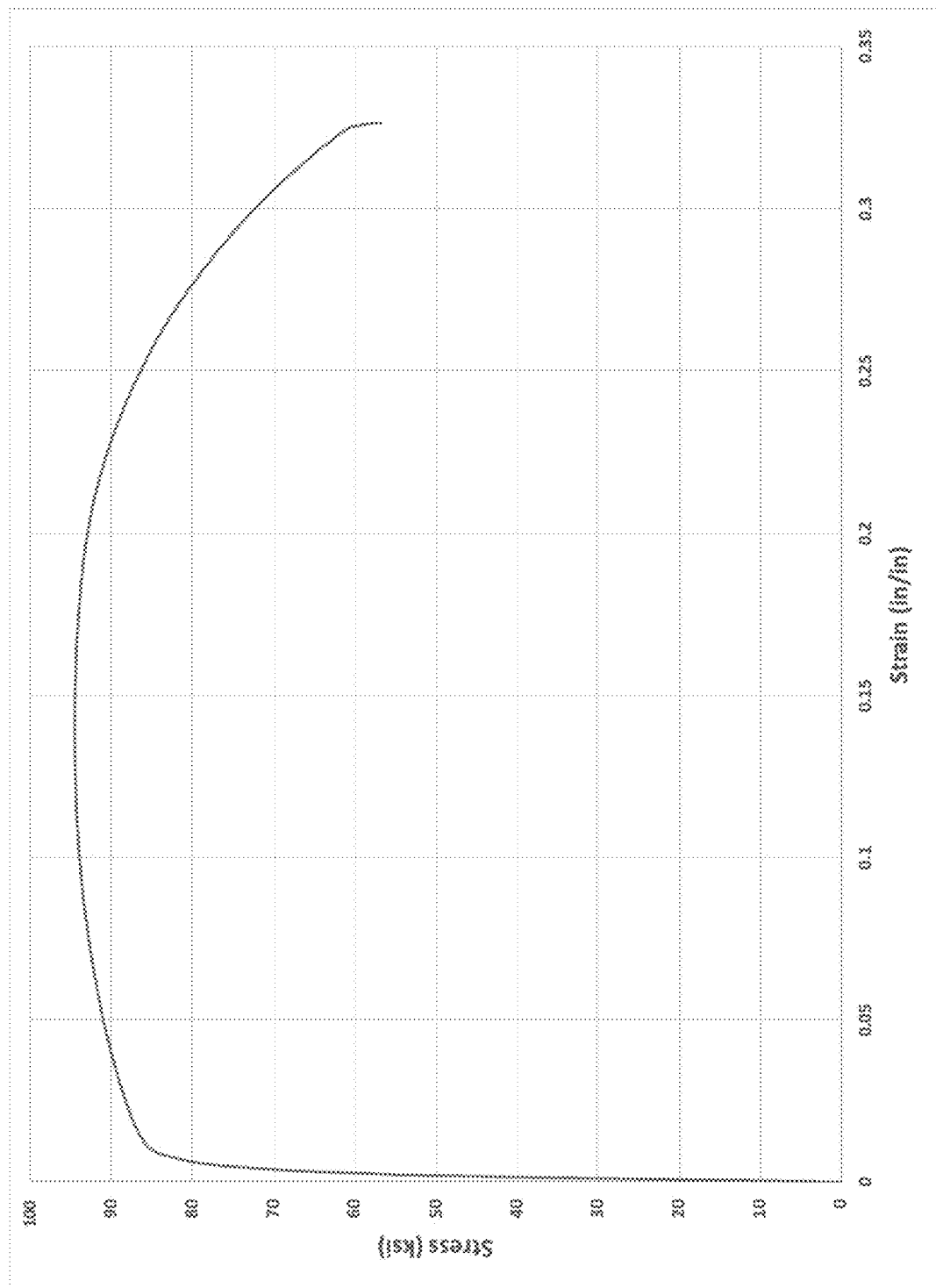
FIG. 6 illustrates testing results of stress vs. strain for a 3D printed tensile test specimen made from the antibacterial stainless steel alloy.

FIG. 6 demonstrates the tensile properties of a test specimen 3D printed from the antibacterial stainless steel alloy. Test procedures followed the ASTM standard. The yield strength in this example specimen was approximately 78 ksi and the tensile strength was approximately 96 ksi. The strain-at-break was approximately 0.326 in./in.

Figure 7:
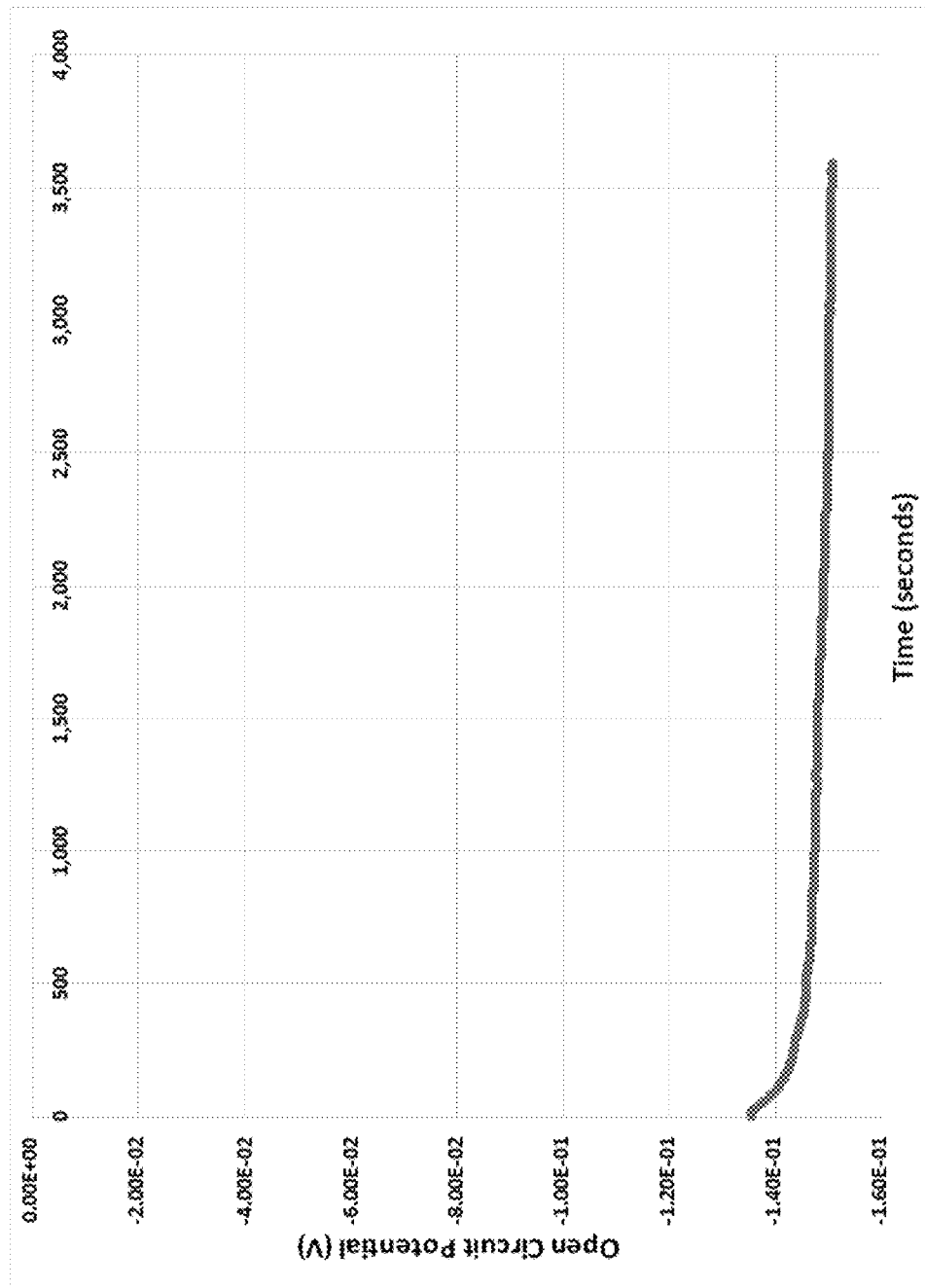
FIG. 7 illustrates that the open circuit potential (OCP) of a test specimen reached quasi-stationary values by 1 hour.
Figure 8:
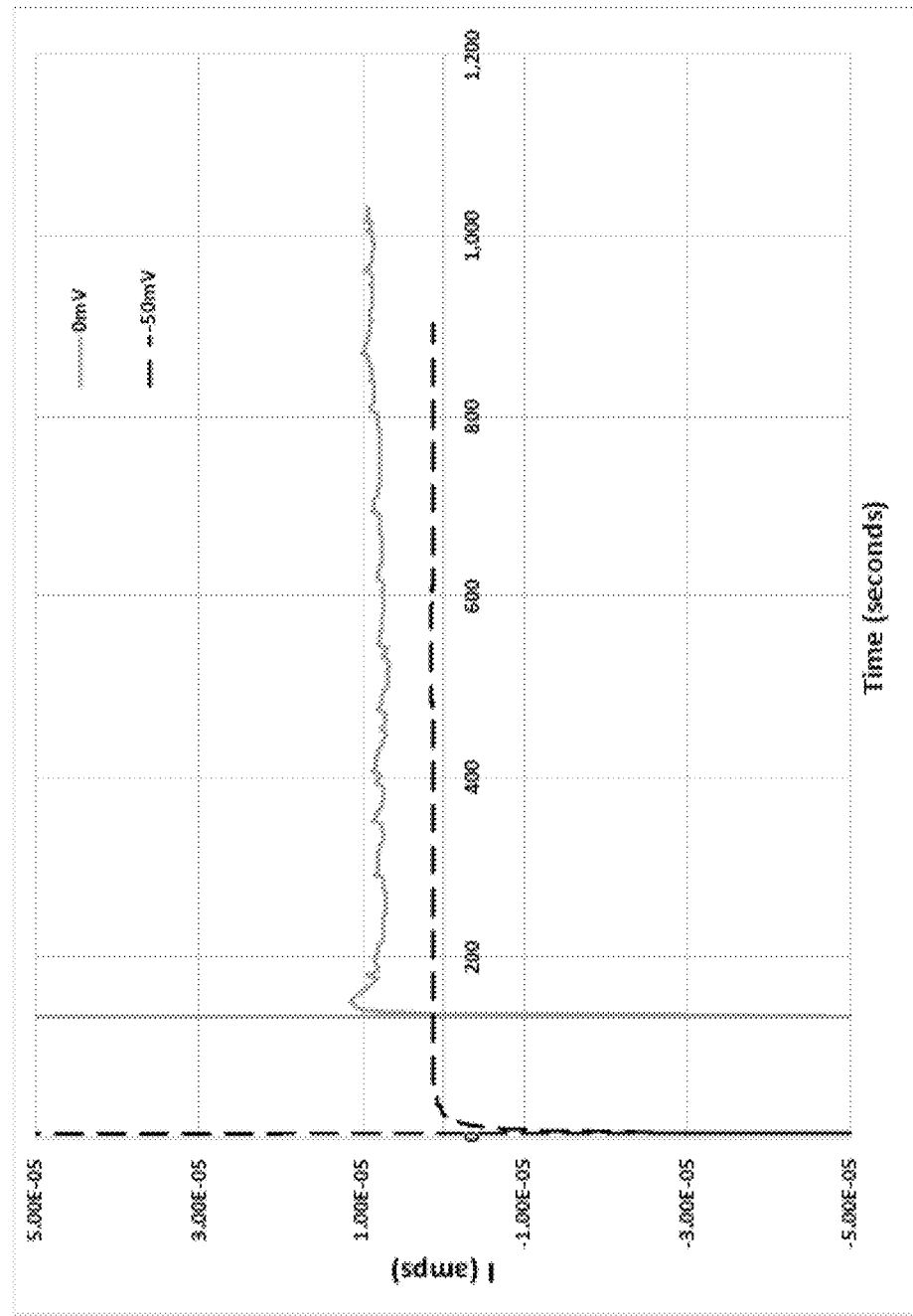
FIG. 8 illustrates the critical pitting potential of the same specimen as in FIG. 7.

Corrosion resistance of the antibacterial stainless steel alloy was tested using a validated electrochemical experimental procedure following the ASTM standard with modified mounting for sample shape. Test specimens were in the form of 12.7 mm diameter disks that were approximately 4 mm thick. The antibacterial stainless steel alloy disks aged at 700° C. for four hours were used as the test specimens. Testing was performed in phosphate buffered saline (PBS) at 37° C. A saturated calomel electrode was used for the reference electrode. An open circuit potential (OCP) test was first performed for 1 hour followed by critical pitting potential testing. FIG. 7 illustrates that the open circuit potential (OCP) of a test specimen reached quasi-stationary values by 1 hour. FIG. 8 illustrates the critical pitting potential of the same specimen as in FIG. 7, where the critical pitting potential for the specimen is −50 mV.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A stainless steel alloy composition consisting of:
3.5-4.5 weight % copper, 18.0-20.0 weight % chromium, 14.0-16.0 weight % nickel, 2.5-3.0 weight % molybdenum, 0.08-0.12 weight % nitrogen, less than 2.0 weight % manganese, less than 0.75 weight % silicon, less than 0.02 weight % carbon, less than 0.025 weight % phosphorous, and less than 0.01 weight % sulfur, and iron as a remaining amount of the stainless steel alloy composition.

2. The stainless steel alloy composition of claim 1, wherein the stainless steel alloy composition is 3D printable.

3. The stainless steel alloy composition of claim 2, wherein the stainless steel alloy composition is 3D printable by at least one of selective laser melting, selective laser sintering, direct metal laser sintering, e-beam melting, and laser engineered net shaping.

4. The stainless steel alloy composition of claim 1, wherein the stainless steel alloy composition is an antibacterial material.

5. The stainless steel alloy composition of claim 1, wherein the stainless steel alloy composition is configured as an orthopedic implant.

6. The stainless steel alloy composition of claim 1, wherein the stainless steel alloy composition comprises a stainless steel alloy powder.

7. The stainless steel alloy composition of claim 6, wherein the stainless steel alloy powder has a range of particle diameters of 15 microns to 45 microns.

8. The stainless steel alloy composition of claim 6, wherein the stainless steel alloy powder has a range of particle diameters of 44 microns to 106 microns.

9. The stainless steel alloy composition of claim 6, wherein the stainless steel alloy powder is produced by one of gas atomization using an inert gas such as nitrogen or argon, plasma atomization, and a plasma rotating electrode processes.

10. The stainless steel alloy composition of claim 1, wherein the composition comprises homogenously distributed nanoscale copper precipitates.

11. The stainless steel alloy composition of claim 1, wherein the stainless steel alloy composition has a Vickers microhardness of 182 to 201 HV/1.

12. The stainless steel alloy composition of claim 1, wherein the stainless steel alloy composition has a Vickers microhardness of 182 to 201 HV/1.

* * * * *